United States Patent [19]

Phillips et al.

[11] Patent Number: 5,082,963
[45] Date of Patent: Jan. 21, 1992

[54] PROCESS FOR THE REGIOSPECIFIC SULFONATION OF SULFONYL SUBSTITUTED 2-AMINONAPHTHALENES AND FIBER REACTIVE AZO DYES MADE FROM THE PRODUCTS OF SAID PROCESS

[75] Inventors: Thomas S. Phillips, West Warwick, R.I.; Anthony J. Corso, Bad Sodena.Tn, Fed. Rep. of Germany

[73] Assignee: Hoechst Celanese Corporation, Somerville, N.J.

[21] Appl. No.: 934,053

[22] Filed: Nov. 24, 1986

[51] Int. Cl.$^5$ .................. C07C 305/12; C07C 313/16
[52] U.S. Cl. ........................ 558/33; 558/61; 534/629; 534/642
[58] Field of Search ............... 534/629, 642; 260/507 R, 505 C; 558/33, 61

[56] References Cited

U.S. PATENT DOCUMENTS

| | | | |
|---|---|---|---|
| 2,657,205 | 10/1953 | Heyna et al. | 260/185 |
| 4,045,428 | 8/1977 | Meininger et al. | 534/642 |
| 4,046,754 | 9/1977 | Meininger et al. | 260/162 |
| 4,110,365 | 8/1978 | Bildstein et al. | 260/505 C |
| 4,118,184 | 10/1978 | Opitz et al. | 534/629 X |
| 4,252,529 | 2/1981 | Steuernagel | 534/629 X |
| 4,334,076 | 6/1982 | Steuernagel et al. | 534/629 X |
| 4,379,937 | 4/1983 | Corso et al. | 546/155 |
| 4,492,654 | 1/1985 | Hoyer et al. | 534/827 |
| 4,600,542 | 7/1986 | Lindner et al. | 260/505 C |

FOREIGN PATENT DOCUMENTS

| | | | |
|---|---|---|---|
| 0064693 | 11/1982 | European Pat. Off. | 260/505 C |
| 0124797 | 11/1984 | European Pat. Off. | 534/642 |
| 0211338 | 7/1984 | German Democratic Rep. | 260/507 R |
| 45-10789 | 4/1970 | Japan | 534/642 |
| 58-164645 | 9/1983 | Japan | 534/642 |
| 59-115360 | 7/1984 | Japan | 534/642 |

OTHER PUBLICATIONS

Cerfontain, "Mechanistic Aspects in Aromatic Sulfonation and Desulfonation", pp. 1 to 45 (1968).

*Primary Examiner*—Mary C. Lee
*Assistant Examiner*—Fiona T. Powers
*Attorney, Agent, or Firm*—Hugh C. Crall

[57] ABSTRACT

A process for the preparation of isomerically pure sulfonic acids of 2-aminonaphthalenes having a fiber reactive substituent of the formula —($SO_2X$) wherein X is —$CH_2$—$CH_2$—Z and Z is a substituent such as thiosulfato, phosphato or sulfato. The process comprises a first step of acylating the amino group of the substituted 2-aminonaphthalene to form a N-acyl derivative of the formula, R—CO—NH—A—$SO_2X$ wherein A represents a naphthalene nucleus. The N-acyl derivative is then sulfonated to provide an essentially isomerically pure sulfonic acid derivative of the formula R—CO—NH—A(—$SO_2X$, —$SO_3H$). Depending upon the position of the —$SO_2X$ group in the starting material, the sulfonation reaction product will have one of the following isomeric ring positions for the sulfonyl and sulfo groups, respectively; 5:7 or 7:5 or 6:8 or 8:6. Exemplary products are 2-acetylamino-5-(beta-sulfatoethylsulfonyl)-naphthalene-7-sulfonic acid or 2-acetylamino-7-(beta-sulfatoethylsulfonyl)-naphthalene-5-sulfonic acid or 2-acetylamino-6-(beta-sulfatoethylsulfonyl)-naphthalene-8-sulfonic acid or 2-acetylamino-8-(beta-sulfatoethylsulfonyl)-naphthalene-6-sulfonic acid. The latter aminonaphthalene sulfonic acid having 2-8-6 substitution is an important starting material for the preparation of fiber reactive dyes; the former three are not. New monoazo and disazo dyes or their metal complexes may be prepared from the 2,6,8; 2,5,7; and 2,7,5 isomers by diacylating, diazotizing and coupling them with coupling components selected from an unsubstituted or substituted benzene, naphthylene, acetoacetic acid arylide, arylamide, pyazolone or pyridone.

12 Claims, No Drawings

PROCESS FOR THE REGIOSPECIFIC SULFONATION OF SULFONYL SUBSTITUTED 2-AMINONAPHTHALENES AND FIBER REACTIVE AZO DYES MADE FROM THE PRODUCTS OF SAID PROCESS

BACKGROUND OF THE INVENTION

Sulfonated naphthylamines containing the fiber reactive beta-hydroxyethylsulfone group or its reactive equivalent are important starting materials in the preparation of fiber reactive, water soluble azo dyestuffs. The sulfonation of such substituted naphthylamines is well known in the art. The sulfonation is carried by reacting the substituted naphthylamine with fuming sulfuric acid (oleum) in sulfuric acid usually at elevated temperature.

It is well known in the literature that the sulfonation of aminonaphthalenes and aminonaphthalene monosulfonic acids results in a mixture of isomeric products; see e.g. Mechanistic Aspects of Aromatic Sulfonation and Desulfonation; Cerfontain, H.; Chapter 7; John Wiley & Sons, New York, N.Y. (1968). Isomeric sulfonation products are also produced when a naphthylamine substituted with the beta-hydroxyethylsulfone group are sulfonated.

These isomeric mixtures of the sulfonation reaction are separated in commercial manufacturing processes by the selective crystallization of one isomer over the other after drowning the reaction solution in ice and water usually containing an inorganic salt such as sodium chloride. For example, the sulfonation of 2-aminonaphthalene-6-hydroxyethylsulfone in sulfuric with oleum at temperature of 70°-80° C. gives rise to two isomeric products; the 1-sulfo and 8-sulfo isomers in a ratio of 95:5 parts, respectively. Upon drowning into ice and water containing sodium chloride, the 1-sulfo isomer is recovered as a precipitate by filtration. A certain portion of the 1-sulfo isomer and essentially all of the 8-sulfo isomer are lost in the filtrate because it is extremely difficult to recover at this point due to its high water solubility.

It is the object of this invention to provide a process of the direct preparation of sulfonated 2-aminonaphthalenes containing fiber reactive, sulfone substituent as a single sulfonation product and new dyestuffs prepared from such substituted 2-aminonaphthalenes.

Although the prior art discloses a general procedure for the preparation of sulfonated aminonaphthalene hydroxyethyl sulfones; see e.g., U.S. Pat. No. 4,046,754, col. 2, lines 59-68, col. 3, lines 1-15; there is no appreciation or recognition in the prior art of the regiospecificity of the process of this invention nor of the properties of dyestuff prepared using the 2-amino-6-(β-hydroxyethylsulfonyl)-naphthalene-8-sulfonic acid. This compound is disclosed at column 3, line 9 of the '754 patent.

SUMMARY OF THE INVENTION

This invention is that of a process for the regiospecific sulfonation of substituted 2-aminonaphthalenes containing a fiber reactive, sulfone substituent. The invention is also that of new water soluble, fiber reactive, azo dyestuffs prepared from said sulfonated 2-aminonaphthalenes.

The sulfonation of substituted and unsubstituted aminonaphthalenes produces a reaction product containing an isomeric mixture of sulfonated aminonaphthalenes. It, however, has been discovered that sulfonyl-substituted 2-aminonaphthalenes can be regiospecifically sulfonated to a single specific sulfonation product by first acylating the amino group of said naphthalenes. The acylated, sulfonyl substituted, aminonaphthalene is then sulfonated to produce a single, specific sulfonation product. The reaction product of the sulfonation can then be deacylated by heating the reaction product to a temperature of about 100°-115° C.

The sulfonated, sulfonyl-substituted, acylamino naphthalenes of the process of this invention have the following general formula:

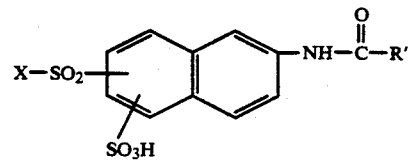

wherein:

R' is an alkyl, aryl or substituted alkyl or substituted aryl group.

The rings subtituents (—SO₂—X) and (—SO₃H) have the following ring positions depending upon the ring position of the sulfonyl substituent:

| (—SO₂—X) | (—SO₃H) |
| --- | --- |
| 5 | 7 |
| 7 | 5 |
| 6 | 8 |
| 8 | 6 |

X is —CH₂—CH₂—Z and Z is an organic or inorganic radical capable of being split off by means of an alkaline agent such as sodium hydroxide.

Although 2-amino-8(β-hydroxyethylsulfonyl)-naphthalene-6-sulfonic acid is a well known starting material for fiber reactive, water soluble azo dyestuff, the 5,7; 7,5; and 6,8 isomers are not. The azo dyestuffs and their metal complexes prepared from the latter isomers have excellent dye properties; especially when used in combination with other dyes (dichromatic and trichromatic dyeings).

DESCRIPTION OF THE PREFERRED EMBODIMENTS

This invention provides a method for the regiospecific sulfonation of aminonaphthalenes containing the fiber reactive sulfonyl group. The invention is also that of new monoazo, disazo dyestuffs and their metal complexes prepared from regiospecifically sulfonated 2-aminonaphthalenes containing a fiber reactive substituted sulfonyl group.

This process for regiospecific sulfonation of substituted aminonaphthalene is illustrated by the following simplified reaction scheme:

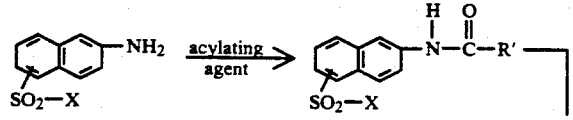

-continued

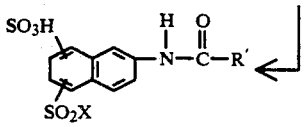

where
X is —CH$_2$—CH$_2$—Z and
Z is an inorganic or organic substituent capable of being split off by an alkaline agent; for example, sodium hydroxide, sodium carbonate or a mixture thereof.

The acylating agent which may be employed in the present process may be any of those currently utilized to acylate aromatic amines. Typical acylating agents are the anhydrides and acid halides such as compounds of the formula:

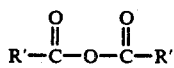

or

wherein Y is halogen, preferably chlorine or bromine and R' is alkyl, aryl or substituted alkyl or aryl. Preferably, R' is lower alkyl of 1 to 4 carbons, phenyl or substituted lower alkyl or substituted phenyl; wherein the substituents may be one or more halo, nitro, lower alkoxy, phenoxy, lower alkyl (if substituted phenyl) phenyl (if substituted alkyl) and combinations thereof; most preferably acetic anhydride, phthalic anhydride and benzoyl chloride.

The acylation reaction may be conducted in aqueous solution or in the solid phase; see, for example, EPO Patent Application 85107751.1, filed June 22, 1985 and U.S. Pat. No.4,379,937, the teachings of which are incorporated herein by reference.

The acylated, sulfonyl-substituted, aminonaphthalene is then sulfonated in sulfuric acid with oleum at room temperature or at temperature between 0°–80° C., preferably between 10°–50° C., most preferably 5°–15° C.

Surprisingly, the regiospecificity of the process of this invention is not found to be present in the sulfonation of 2-aminonaphthalene sulfonic acids or 1-aminonaphthalene 5 or 6 β-hydroxyethyl sulfones. Although acylation prior to sulfonation did result in some narrowing of the isomer distribution, this result was not found in all cases and an isomeric mixture was obtained in all instances. Thus, the regiospecificity of the process of the invention has been found to be present only in the 2-aminonaphthylamines containing the fiber reactive group (X—SO$_2$—).

The following table illustrates the regiospecificity of the process of this invention:

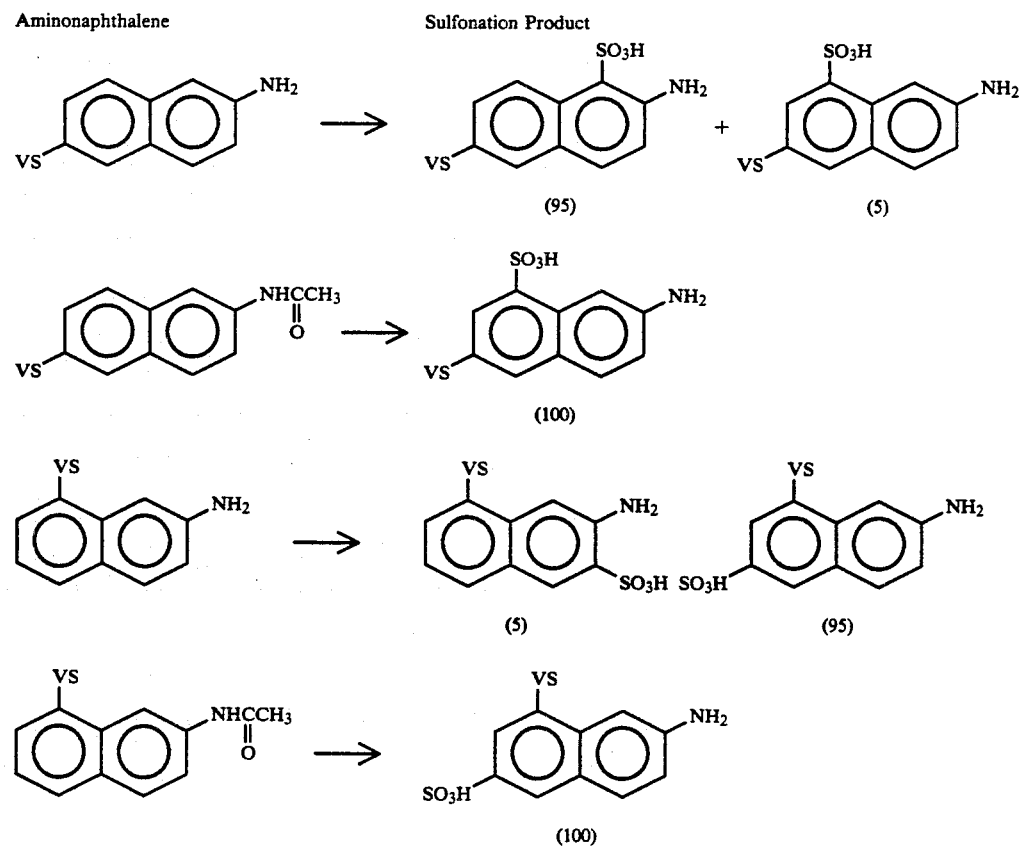

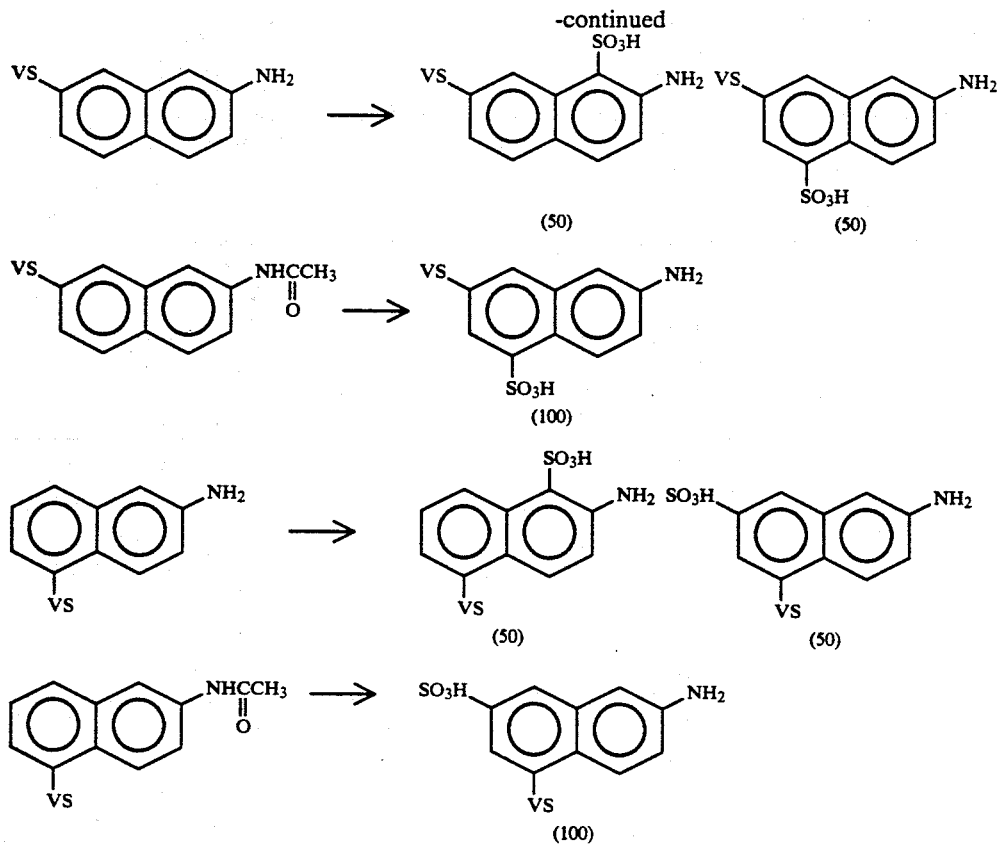

Vs in the above table represents the beta-sulfatoethylsulfonyl) group

As can be seen from the above table, the following products can be prepare by the process of this invention in essentially pure form, free of other isomeric reaction products:

2-amino-6-(beta-sulfatoethylsulfonyl)-naphthalene-8-sulfonic acid
2-amino-8-(beta-sulfatoethylsulfonyl)-naphthalene-6-sulfonic acid
2-amino-7-(beta-sulfatoethylsulfonyl)-naphthalene-5-sulfonic acid
2-amino-5-(beta-sulfatoethylsulfonyl)-naphthalene-7-sulfonic acid It will be readily apparent to one skilled in the art that the β-sulfatoethylsulfonyl group may be replaced with another fiber reactive moiety represented by the general formula —CH$_2$—CH$_2$—Z wherein Z is an inorganic or organic substituent which can be split off by the action of an alkaline reagent such as sodium hydroxide, sodium carbonate, etc. Replacement of the sulfato leaving group can be done either prior to or subsequent to sulfonation depending upon the reactivity of leaving group to the sulfonation step. Examples of other leaving substituents (Z) are halogen atoms such as chlorine or bromine; hydroxy, an acyloxy group such as the acetoxy group; a dialkylamino group such as the dimethylamino or diethylamino group; the thiosulfato or the phosphato group; preferably the leaving group is the sulfato group. Similarily, the fiber-reactive group may converted its vinyl form (—CH=CH$_2$) after the dyestuff has been prepared. When the fiber-reactive group comprises the vinyl form in the following description, the designation X' is used.

The 2-amino-8-(β-sulfatoethylsulfonyl)-naphthalene-6-sulfonic acid is an important aminonaphthalene used in the preparation monoazo and disazo dyestuff; see, for example, U.S. Pat. No. 4,046,475. The ability to produce it as a pure single reaction product presents cost saving opportunity and a better starting material since residual contamination with the 3-sulfo isomer can cause a hypsochromic shift in the resulting dyestuff.

The process of this invention comprises sulfonating an acylated, 2-aminonaphthalene containing the fiber reactive group X—SO$_2$—; i.e., N-acyl-2-amino-(beta-X—SO$_2$—)-naphthalene. The group X—SO$_2$— being as previously defined. The sulfonation of these N-acylated-2-aminonaphthalenes results in a single specific sulfonation product.

The sulfonation can be conducted by any of the known methods for sulfonating an acylated-aminonaphthalene. Common sulfonating agents include fuming sulfuric acid, sulfur trioxide, chlorosulfonic acid, etc. Preferably the sulfonation is conducted in a sulfuric acid reaction medium with oleum (fuming sulfuric acid).

The N-acyl-2-amino-(beta-X—SO$_2$) naphthalene are preferably N-acyl-2-aminonaphthalenes containing the fiber reactive substitutent (X—SO$_2$—) in the 5, 6, 7 or 8 ring position. The group (X—SO$_2$—) is preferably the beta chloro or bromo ethyl sulfonyl; beta-hydroxyethyl sulfonyl; beta-sulfatoethylsulfonyl; beta-phosphatoethylsulfonyl; beta-thiosulfatoethylsulfonyl; most preferably beta-hydroxyethylsulfonyl or beta-sulfatoethylsulfonyl.

Preferably, the sulfonation is conducted by dissolving the (X—SO$_2$—) substituted N-acylated-2-aminonaphthalene in sulfuric acid at a temperature of 0°–50° C.; preferably between 10°–15° C. to reduce the possibility of deacylating the reactant. The acylated compound is then sulfonated at 10°-50° C., preferably at 10°-15° C. by treatment with oleum.

After completing the sulfonation, the sulfonation product may be deacylated or recovered in the N-acyl form. Deacylation can be conducted by any known method, preferably by the addition of water to the reaction product and heating. For example, by dilution with water until the sulfuric acid concentration is between 85-100 percent, preferably 95-98%. After adjusting the acid concentration, the reaction mixture is heated to 80°-120° C., preferably 100°-110° C. to effect the deacylation.

The use of the other isomers, i.e., 2-amino-6-(β-sulfatoethylsulfonyl)-naphthalene-8-sulfonic acid, 2-amino-7-(β-sulfatoethylsulfony)-naphthalene-5-sulfonic acid and 2-amino-5-(β-sulfatoethylsulfonyl)-maphthalene-7-sulfonic acid has not been found to be present in the art. Although U.S. Pat. No. 4,046,754 suggests the use of the 2-amino-6-(β-hydroxyethylsulfonyl)-naphthalene-8-sulfonic acid as a diazotizable amine in the preparation of water soluble, fiber reactive monoazo dyestuffs, however, no specific dyestuffs from this base are reported. Surprisingly, this base (the 2-amino-6-sulfonyl-8-sulfo) gives most interesting azo dyestuffs with superior properties which include unique non-blocking characteristics i.e., these dyes do not block nor are they blocked when used in combination with other dyes which is the usual commercial practice.

It is the object of this invention to produce new and useful monozo and disazo dyestuffs and their metal complexes from the following substituted aminonaphthalenes represented by the general formula (in the free acid form) (1):

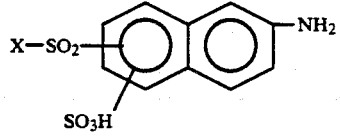

wherein the substituents X—SO2— and SO3H have the following respective ring positions:

| —SO2—X | HSO3— |
|---|---|
| 6 | 8 |
| 5 | 7 |
| 7 | 5 |

Monoazo dyestuffs prepared from the above diazotizable amineshave the following general formula (2) in the free acid form:

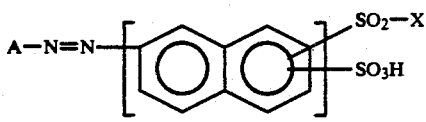

wherein the ring position is specified above for the —SO3H and —SO2—X' groups. Diazotization is carried out by known methods; i.e., by the treatment of the amine with sodium nitrite in the presence of mineral acids or by treatment with nitrosyl sulfuric acid.

The group "A" represents the residue of a coupling component of the benzene, naphthalene, acetoacetic acid anilide or naphthylide arylamide, pyrazolone or pyridone series. Specific examples of such coupling components follow.

The coupling component may be an acetoacetic acid anilide or naphthylide having the following general formulas:

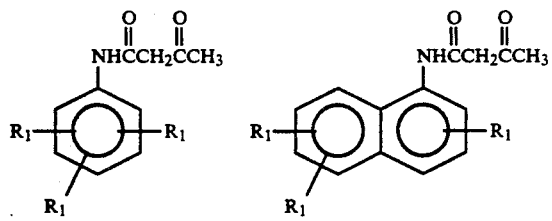

These coupling components may be substituted in the aromatic nucleus by the substituent $R_1$ which is independently selected from hydroxy, chloro, bromo, lower alkyl or alkoxy of 1-4 carbons, sulfo or —SO2—X wherein X is as previously defined or (—CH2=CH2).

The coupling component may also be selected from substituted or unsubstituted α or β naphthols such as mono- and dihydroxy naphthalenes having the following general formula:

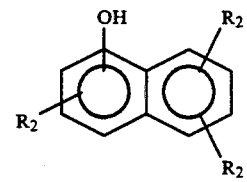

wherein the substituent $R_2$ is independently selected from hydrogen, lower alkyl, lower alkoxy, amino, N-acylamino of 1 to 4 carbons, N-alkylamino of 1 to 4 carbons, (5-chloro-2,4,6-triazene-1-yl)-amino and sulfo.

Further examples of the coupling component include:

A substituted or unsubstituted pyrazolones, especially 5-pyrazolones which couple in the 4 position and which, if substituted, are substituted in the 3 position by lower alkyl, lower alkoxy or carboxy and in the 1 position by substituted or unsubstituted phenyl. Substituents for the phenyl ring are selected from sulfo, chloro, bromo, hydroxy, or —SO2—X.

A substituted or unsubstituted arylamine of the formula:

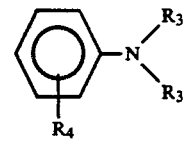

wherein $R_3$ is independently selected from lower alkyl, lower alkoxy and hydrogen and $R_4$ is selected from hydroxy, chloro, bromo, sulfo, N,N-dialkylamino, N-alkylamino, N-acylamino having 1 to 4 carbons and —SO2—X.

Pyridone optionally substituted in the 2-position with a substituent selected from lower alkyl, lower alkoxy, carboxy and cyano and in the 1-position by substituted or unsubstituted alkyl or phenyl wherein said phenyl ring substituents are independently selected from chloro, bromo, hydroxy, sulfo or —SO2—X.

Preferred coupling components for the preparation of mono-azo dyestuffs of the invention are:
1-acetoacetylamino-3-methyl-6-methoxybenzene-4-sulfonic acid; 1-actoacetylamino-3,6-dimethoxybenzene-4-sulfonic acid; 1-hydroxynaphthalene-3,6-disulfonic acid; 1-hydroxynaphthalene-4-sulfonic acid; 1-acetylamino-8-hydroxy-naphthalene-3,6-disulfonic acid; 1-acetylamino-8-hydroxy-napthalene-3,5-disulfonic acid; 1-benzoylamino-8-hydroxy-naphthalene-3,6-disulfonic acid; 1-benzoylamino-8-hydroxy-naphthalene-3,5-disulfonic acid; 2-acetylamino-5-hydroxy-naphthalene-7-sulfonic acid; 3-acetylamino-5-hydroxy-naphthalene-7-sulfonic acid; 1-(4'-sulfophenyl)-3-methyl-5-pyrazolone; 1-(4'-sulfophenyl)3-carboxy-5-pyrazolone; 1-(4'-[2-sulfooxyethyl)phenyl]-sulfonyl)-3-methyl-5-pyrazolone; N,N-bis-(2-sulfooxyethyl)-3-chloroaniline; N-(2-ethanesulfonic acid)-4-methyl-6-hydroxypyridone; and 1-hydroxynaphthalene-3,6-disulfonic acid-8-(5-chloro-2,4,6-triazene-1-yl)-amino.

Most preferred coupling components are 1-acetoacetylamino-3-methyl-6-methoxybenzene-4-sulfonic acid; 1-hydroxynaphthalene-3,6-disulfonic acid; 1-hydroxynaphthalene-4-sulfonic acid; 1-acetylamino-8-hydroxy-naphthalene-3,6-disulfonic acid; 1-acetylamino-8-hydroxy-napthalene-3,5-disulfonic acid; 1-benzoylamino-8-hydroxy-naphthalene-3,6-disulfonic acid; 1-benzoylamino-8-hydroxy-naphthalene-3,5-disulfonic acid; 2-acetylamino-5-hydroxy-naphthalene-7-sulfonic acid; 1-hydroxynaphthalene-3,6-disulfonic acid-8-(5-chloro-2,4,6-triazene-1-yl)-amino.

The naphthylamine bases of this invention are also useful in the preparation of disazo, fiber reactive dyestuffs and their metal complexes. These disazo compounds correspond to the following general formula (3):

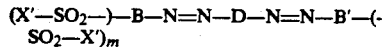

wherein
B is selected from a 2-amino-naphthalene-8-sulfonic acid nucleus wherein the fiber reactive group X'—SO$_2$— is substituted in the 6-position of said nucleus; the 2-amino-napthalene-5-sulfonic acid nucleus; wherein the fiber reactive group X'—SO$_2$— is substituted in the 7-position of the naphthalene nucleus and 2-amino-naphthalene-7-sulfonic acid nucleus wherein the fiber reactive group X'—SO$_2$— is substituted in the 5-position of said nucleus;

B' is equal to B or is selected from a benzene or naphthalene nucleus which can be substituted by one to three substituents independently selected from chloro, fluoro, bromo, sulfo, carboxy, lower alkoxy, lower alkyl, N-acylamino, N-alkylamino, N,N-dialkyl and (5-chloro-2,4,6-triazene-1-yl)-amino-5-triazinyl-amino. The term "m" is an integer equal to 0 or 2 and X' is as was previously defined.

D represents a substituted benzene or naphthalene nucleus containing at least one hydroxy substituent and it may be further substituted with 1 to 4 substituents independently selected from chloro, fluoro, bromo, sulfo, carboxy, lower alkoxy, lower alkyl, N-acylamino of 1 to 6 carbons, N-acylamino of 1 to 4 carbons, N,N-dialkylamino of 2 to 8 carbons.

The diazo compounds according to general formula (3) are prepared by known method; see, for example, U.S. Pat. Nos. 2,657,205 and 4,492,654 which are hereby incorporated by reference. The preparation of such disazo dyestuff is fully explained in said patent; see specifically Column 3 and 4 of U.S. Pat. No. 4,492,654.

The groups B and B' are provided by diazotization of the aromatic amine starting material by known procedures, for example, in acidic, aqueous medium with sodium nitrite at a temperature between −5° C. and 15° C. One of these diazonium salts is then coupled to an aromatic compound represented by the formula H-D-H wherein H respresents hydrogen substituents. The first coupling is usually conducted under acidic conditions at pH from about 1 to about 3 at a temperature of about 5°-30° C. The second coupling in then effected at a higher pH in the range of 4-8, preferably 5-7 and temperature of about 5°-30° C.

The group B represents the residue of a diazonium salt prepared from a substituted-2-aminonaphthalene having the general formula (1) herein previously defined.

The group B' represents the residue of a diazonium salt identical to B or substituted or unsubstituted aromatic amine previously defined. Examples of such other aromatic amines are:
2-bromo-4-(β-sulfatoethylsulfonyl)-aniline; 2-fluoroaniline; 2-bromo-aniline; 2-methoxy-5-methyl-4-(β-sulfatoethylsulfonyl)-aniline; 3-(β-sulfatoethylsulfonyl)-aniline; 2-chloro-4-(β-sulfatoethylsulfonyl)-aniline; 2-nitro-4-(β-sulfatoethylsulfonyl)-aniline; 2-sulfo-4-(β-sulfatoethylsulfonyl)-aniline; 4-vinylsulfonyl-aniline; 4-(β-chloroethylsulfonyl)-aniline; 4-(β-thiosulfatoethylsulfonyl)-aniline; 4-(β-acetoxyethylsulfonyl)-aniline; 4-(β-benzoyloxyethyl-sulfonyl)-aniline; 2-chloroaniline; 2,4-dichloroaniline; 4-amino-benzoic acid; aniline-2-sulfonic acid; Aniline-2-sulfonic acid; Aniline-3-sulfonic acid; Aniline-4-sulfonic acid; Aniline-2,4-disulfonic acid; Aniline-2,5-disulfonic acid; 2-aminonaphthalene-1,5-disulfonic acid; 2-chloroaniline-5-sulfonic acid; 4-(β-sulfatoethylsulfonyl)-aniline; 3-(β-sulfatoethylsulfonyl)-4-methoxy-aniline; 2-methoxy-5-methyl-4-(β-sulfatoethylsulfonyl)-aniline; 2,5-dimethoxy-4-(β-sulfatoethylsulfonyl)-aniline; 4-(β-sulfatoethylsulfonyl)-1-aminonaphthalene; 8-(β-sulfatoethylsulfonyl)-2-aminonaphthalene; 8-(β-sulfatoethylsulfonyl)-2-aminonaphthalene-6-sulfonic acid; 6-(β-sulfatoethylsulfonyl)-2-aminonaphthalene; 6-(β-sulfatoethylsulfonyl)-2-aminonaphthalene- 1-sulfonic acid; 2-aminobenzene sulfonic acid-4-(5-chloro-2,4,6-triazene-1-yl)-amino.

Exemplary divalent couplers (D) are 1-amino-8-naphthol-3,6-disulfonic acid; 1,8-dihydroxynaphthalene; 3,6-sulfonic acid; 1,3-dihydroxybenzene; 1-amino-8-naphthol-3,5-disulfonic acid.

The copper, nickel, chromimum and cobalt metal complexes of the dyes of general formula (2) and (3) can be prepared by known methods from the ortho, ortho' dihydroxyazo dye or the reactive equivalent thereof; e.g., o-alkoxy-o'-hydroxy-azo dyes or by treating an o'hydroxyazo dye, which contains a hydrogen atom in the ortho position to the azo group, with a metal and an oxidizing agent such as hydrogen peroxide in a weakly acid solution. U.S. Pat. No. 4,400,317 for instance describes a method of preparing the metal complex by treatment with non-salt forming metals. The metal complexes dyes of the invention may contain one complexed metal atom to one dye molecule or one metal atom to two dye molecules. In the case of chromimum or cobalt complexes the ratio of metal atoms to dye molecules is preferably 1:2 respectively and in the case of copper and nickel the ratio is 1:1 respectively.

The following examples illustrate the invention. Parts and percentages are by weight unless stated otherwise.

EXAMPLE

This example illustrates the preparation 2-amino-6-(β-sulfatoethylsulfonyl)-naphthalene-8-sulfonic acid. Into a 500 ml round bottom flask equipped with a mechanical stirrer, thermometer and drying tube were charged 162 grams of sulfuric acid monohydrate at a temperature of approximately 15° C. Then 73.3 grams of 2-acetoaminoNaphthalene-6-βhydroxyethyl-sulfone were slowly added over a four hour period. The reaction mixture was then stirred at about 15° C. for one additional hour and then 100 grams of 65% oleum were added. After completing the oleum addition, the reaction mixture was allowed to warm to room temperature at which point the sulfonation reaction was complete.

Approximately 14 grams of ice were added to the reaction mixture and it was then heated under agitation to 100°-110° C. for two hours to effect deacetylation. The reaction mixture was then cooled to 25° C. and drowned onto 250 grams of water, sodium chloride and ice. The reaction mixture was stirred for one half hour, filtered and washed with a cold 20% sodium chloride solution. 147.3 grams of wet press cake were obtained containing 71.6 grams of 2-amino-6-(β-sulfatoethylsulfonyl)-naphthalene-8-sulfonic acid. No other isomeric sulfonation reaction products were detected in the reaction product or the wet press cake.

EXAMPLE 2

This example illustrates the preparation 2-amino-8-(β-sulfatoethylsulfonyl)-naphthalene-6 sulfonic acid. Into a 250 ml round bottom flask equipped with a mechanical stirrer, thermometer and drying tube were charged 162.0 grams of sulfuric acid monohydrate at a temperature of approximately 10° C. Then 73.5 grams of 2-N-acetylaminonaphthalene-8-β-hydroxyethylsulfone (99.6%, M.W. 293.0=0.25 mole) were added over two hours. The reaction mixture was stirred at about 10° C. for two additional hours and then 100.0 grams of 65% oleum were charged over one hour while maintaining the temperature at approximately 10° C. The reaction mixture was allowed to warm to room temperature at which point the sulfonation reaction was complete.

Approximately 14.5 grams of ice were added to the reaction mixture and it was then heated to 100°-110° C. for two hours to effect deacetylation. The reaction mixture was then cooled to 20° C. and added to an aqueous solution containing 250.0 grams of water, 125 grams of sodium chloride and ice in an amount sufficient to keep the temperature at 0° C. The reaction mixture was stirred for one half hour, filtered and washed with a cold 20% sodium chloride solution. 381.8 grams of wet press, cake were obtained containing 88.2 grams of 2-amino-8(β-sulfatoethyl)-sulfonyl)-naphthalene-6-sulfonic acid. No other isomeric sulfonation product were detected in reaction mixture or the isolated press cake.

EXAMPLE 3

This example illustrates the preparation 2-amino-7-(β-sulfatoethylsufonyl)-naphthalene-5-sulfonic acid.

Into a 250 ml round bottom flask equipped with a mechanical stirrer, thermometer and drying tube were charged 65.0 grams of sulfuric acid monohydrate at a temperature of approximately 10° C. Then 29.6 grams of 2-N-acetylaminonaphthalene-7-β-hydroxyethylsulfone (98.9%, M.W. 293.0=0.10 mole) were slowly added over a two hour period. The reaction mixture was then stirred at about 10° C. for one additional hour and then 35.0 g of 65% oleum were added. After completing the oleum addition, the reaction mixture was allowed to warm to room temperature at which point the sulfonation reaction was complete.

Approximately 5.8 grams of ice were added to the reaction mixture and it was then heated to 100°-110° C. for three hours to effect deacetylation. The reaction mixture was then cooled to about 15° C. and drowned into to 100.0 grams of water containing 100 grams of sodium chloride and ice in an amount sufficient to maintain the temperature at 0° C. The product was totally water-soluble and would not precipitate even with the addition of sodium chloride. The pH of the solution was adjusted to 4–4.5 by the addition of 118.0 g sodium carbonate, cooled to about 10° C. and then filtered to remove the precipitated sodium sulfate. The resulting solution which contained the 2-aminonaphthalene-7-(β-sulfatoethylsulfonyl)-5-sulfonic acid was retained for future use. Analysis of the solution showed the yield to be 75% of theoretical.

EXAMPLE 4

This example illustrates the preparation 2-amino-5-(β-sulfatoethylsulfonyl)-naphthalene-7-sulfonic acid. Into 250 ml round bottom flask equipped with a mechanical stirrer, thermometer and drying tube were charged 82.0 grams of sulfuric acid monohydrate at a temperature of approximately 10° C. Then 36.9 grams of 2-N-acetylaminoNaphthalene-5-β-hydroxyethylsulfone (99.0%, M.W. 293.0=0.125 mole) were slowly added over a two hour period. The reaction mixture was then stirred at about 10° C. for one additional hour and then 50.0 grams of 65% oleum were added. After completing the oleum addition, the reaction mixture was allowed to warm to room temperature at which point the sulfonation reaction was complete.

Approximately 7.2 grams of ice were added to the reaction mixture and it was then heated to 100°-110° C. for two hours to effect deacetylation. The reaction mixture was then cooled to approximately 20° C. and added to a mixture of 125 grams of water, 125 grams of sodium chloride and ice in an amount sufficient to maintain the temperature at 0° C. The product was totally water-soluble at this point. The pH was adjusted to 4.0–4.5 with 180.0 grams of sodium carbonate, cooled to 10° C. and filtered to remove the precipitated sodium sulfate. The resulting solution which contained the 2-amino-5-(β-sulfatoethylsulfonyl)-naphthalene-7-sulfonic acid was retained for future use.

EXAMPLE 5

A dyestuff of the following formula in its free acid form was prepared:

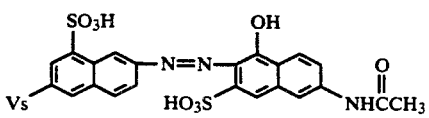

wherein Vs=HO₃SOCH₂CH₂SO₂—

Into a 2 liter beaker equipped with a mechanical stirrer, thermometer and pH probe were added 500 ml of water and 144 grams of a wet presscake containing 82.2 grams of 2-amino-8-sulfonaphthalene-6-(2-sulfooxyethyl)sulfone. The slurry was stirred for two hours and cooled to 0°-5° C. While maintaining the temperature at 0°-5° C. and pH less than 2, 35 grams of a 40% solution of sodium nitrite were added over one hour. The reaction was stirred for one hour with a slight excess of nitrite present. The excess nitrite was decomposed by the addition of 1 gram of sulfamic acid.

756 grams of a solution containing 56.2 grams of 7-acetamino-4-hydroxy-2-naphthalene sulfonic acid were added to the reaction mixture and the pH was adjusted to 5.0-5.5 by the addition of 142 grams of 15% sodium carbonate solution. The resulting solution was dried to yield 221 grams of an orange dyestuff having a strength of 72:100 (i.e. 72 parts of the dyestuff so obtained were equal in strength to 100 parts of standard strength dyestuff).

EXAMPLE 6

A dyestuff of the following formula in its free acid form was prepared:

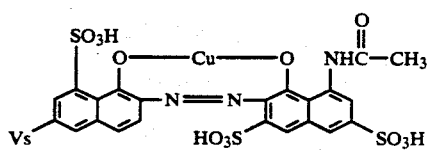

wherein Vs=HO₃SOCH₂CH₂SO₂—

Into a 4 liter equipped with a mechanical stirrer, thermometer and pH probe were added 500 ml of water and 200 grams of a press cake containing 82.2 grams of 2-amino-8-sulfo-naphthalene-6-(2-sulfooxyethyl)sulfone. The slurry was stirred for two hours and then cooled to 0°-5° C. While maintaining the temperature at 0°-5° C. and pH less than 2, 35 grams of a 40% solution of sodium nitrite were added over one hour. The reaction was stirred for one hour with a slight excess of nitrite present. The excess nitrite was decomposed by the addition of 1 gram of sulfamic acid.

442 grams of a solution containing 72.2 grams of 4-hydroxy-5-acetamino-naphthalene-2,7-disulfonic acid were added and the pH of the reaction adjusted to 5.0-5.5 by the addition of 105 grams of a 15% solution of sodium carbonate. Then 250 grams of a 20% solution of copper sulfate pentahydrate were added and over 2 hours, 100 grams of 30% hydrogen peroxide were added while maintaining the pH at 5.0-5.5 by the addition of 15 grams of sodium carbonate.

250 grams of potassium chloride were added, the reaction stirred overnight and filtered. The resulting presscake was dried to yield 108.0 grams of blue dyestuff having a strength of 80:100 (i.e. 80 parts of the dyestuff so obtained were equal in strength to 100 parts of standard strength dyestuff).

EXAMPLE 7

A dyestuff of the following formula in its free acid form was prepared:

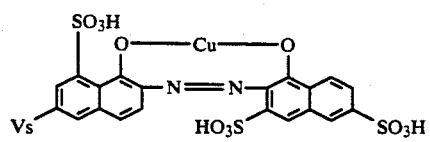

Vs=HO₃SOCH₂CH₂SO₂—

This dyestuff was prepared substantially in accordance with the procedure of Example 6 except the coupling component used was 1-hydroxynaphthalene-3,6-disulfonic acid. The resulting dyestuff was of a blue shade.

EXAMPLE 8

A dyestuff of the following formula in its free acid form was prepared:

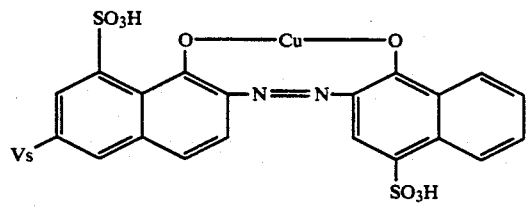

Vs=HO₃SOCH₂CH₂SO₂—

This dyestuff was prepared substantially in accordance with the procedure of Example 6 except the coupling component was 1-hydroxynaphthalene-4-sulfonic acid. The resulting dyestuff was of a blue shade.

EXAMPLE 9

A dyestuff of the following formula in its free acid form was prepared:

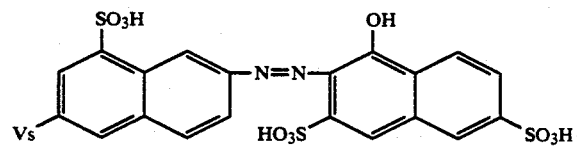

wherein Vs=HO₃SOCH₂CH₂SO₂—

This dyestuff was prepared substantially in accordance with Example 7 except the coppering step was not conducted. The resulting dyestuff was of a scarlet shade.

EXAMPLE 10

A dyestuff of the following formula in its free acid form was prepared:

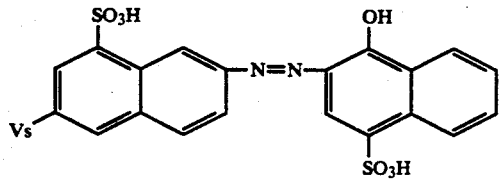

wherein Vs=HO₃SOCH₂CH₂SO₂—

This dyestuff was prepared in accordance with the procedure of Example 8 except the coppering step was not done. The resulting dyestuff was of a scarlet shade.

Other useful dyestuffs with similar dyeing properties can be obtained when in the above examples the 2- amino-6-(β-sulfatoethylsulfonyl)-naphthalene-8-sulfonic acid is replaced with either the 2-amino-7-(β-sulfatoethylsulfonyl)-naphthalene-5-sulfonic acid or the 2-amino-5-(β-sulfatoethylsulfonyl)-naphthalene-7-sulfonic acids and they are coupled with a coupling component set forth in the following table.

The following table illustrates these dyestuffs as well as additional dyestuffs based on the 2-amino-6-(β-sulfatoethylsulfonyl)-naphthalene-8-sulfonic acid.

| Naphthylamine Base | Coupler | Shade |
|---|---|---|
| 2-amino-5-(β-sulfatoethylsulfonyl)-naphthalene-7-sulfonic acid | 1-acetoacetylamino-3-methyl-6-methoxybenzene-4-sulfonic acid | yellow |
| 2-amino-5-(β-sulfatoethylsulfonyl)-naphthalene-7-sulfonic acid | 1-acetoacetylamino-3,6-dimethoxybenzene-4-sulfonic acid | yellow |
| 2-amino-5-(β-sulfatoethylsulfonyl)-naphthalene-7-sulfonic acid | 1-hydroxynaphthalene-3,6-disulfonic acid | orange |
| 2-amino-5-(β-sulfatoethylsulfonyl)-naphthalene-7-sulfonic acid | 1-hydroxynaphthalene-4-sulfonic aicd | scarlet |
| 2-amino-5-(β-sulfatoethylsulfonyl)-naphthalene-7-sulfonic acid | 1-acetylamino-8-hydroxy-naphthalene-3,6-disulfonic acid | red |
| 2-amino-5-(β-sulfatoethylsulfonyl)-naphthalene-7-sulfonic acid | 1-acetylamino-8-hydroxy-napthalene-3,5-disulfonic acid | red |
| 2-amino-5-(β-sulfatoethylsulfonyl)-naphthalene-7-sulfonic acid | 1-benzoylamino-8-hydroxy-naphthalene-3,6-disulfonic acid | red |
| 2-amino-5-(β-sulfatoethylsulfonyl)-naphthalene-7-sulfonic acid | 1-benzoylamino-8-hydroxy-naphthalene-3,5-disulfonic acid | red |
| 2-amino-5-(β-sulfatoethylsulfonyl)-naphthalene-7-sulfonic acid | 2-acetylamino-5-hydroxy-naphthalene-7-sulfonic acid | orange |
| 2-amino-5-(β-sulfatoethylsulfonyl)-naphthalene-7-sulfonic acid | 3-acetylamino-5-hydroxy-naphthalene-7-sulfonic acid | scarlet |
| 2-amino-5-(β-sulfatoethylsulfonyl)-naphthalene-7-sulfonic acid | 1-(4'-sulfophenyl)-3-methyl-5-pyrazolone | yellow |
| 2-amino-5-(β-sulfatoethylsulfonyl)-naphthalene-7-sulfonic acid | 1-(4'-sulfophenyl)-3-carboxy-5-pyrazolone | yellow |
| 2-amino-5-(β-sulfatoethylsulfonyl)-naphthalene-7-sulfonic acid | 1-(4'-[2-sulfooxyethyl)phenyl]sulfonyl)-3-methyl-5-pyrazolone | yellow |
| 2-amino-5-(β-sulfatoethylsulfonyl)-naphthalene-7-sulfonic acid | N,N-bis-(2-sulfooxyethyl)-3-chloroaniline | orange |
| 2-amino-5-(β-sulfatoethylsulfonyl)-naphthalene-7-sulfonic acid | N-(2-ethanesulfonic acid)-4-methyl-6-hydroxy-pyridone | yellow |
| 2-amino-5-(β-sulfatoethylsulfonyl)-naphthalene-7-sulfonic acid | 1-hydroxynaphthalene-3,6-disulfonic acid copper complex | blue |
| 2-amino-5-(β-sulfatoethylsulfonyl)-naphthalene-7-sulfonic acid | 1-hydroxynaphthalene-4-sulfonic acid copper complex | blue |
| 2-amino-5-(β-sulfatoethylsulfonyl)-naphthalene-7-sulfonic acid | 1-acetylamino-8-naphthol-3,6-disulfonic acid copper complex | blue |
| 2-amino-5-(β-sulfatoethylsulfonyl)-naphthalene-7-sulfonic acid | N,N-bis(2-sulfatoethyl)-meta-chloro-aniline | orange |
| 2-amino-5-(β-sulfatoethylsulfonyl)-naphthalene-7-sulfonic acid | N,N-bis(2-sulfatoethyl) aniline | orange |
| 2-amino-5-(β-sulfatoethylsulfonyl)-naphthalene-7-sulfonic acid | 1-hydroxynaphthalene-3,6-disulfonic acid-8-(5-chloro-2,4,6-triazene-1-yl)-amino. | red |
| 2-amino-6-(β-sulfatoethylsulfonyl)-naphthalene-8-sulfonic acid | 1-acetoacetylamino-3-methyl-6-methoxybenzene-4-sulfonic acid | yellow |
| 2-amino-6-(β-sulfatoethylsulfonyl)-naphthalene-8-sulfonic acid | 1-acetoacetylamino-3,6-dimethoxybenzene-4-sulfonic acid | yellow |
| 2-amino-6-(β-sulfatoethylsulfonyl)-naphthalene-8-sulfonic acid | 1-hydroxynaphthalene-3,6-disulfonic acid | orange |
| 2-amino-6-(β-sulfatoethylsulfonyl)-naphthalene-8-sulfonic acid | 1-hydroxynaphthalene-4-sulfonic acid | scarlet |
| 2-amino-6-(β-sulfatoethylsulfonyl)-naphthalene-8-sulfonic acid | 1-acetylamino-8-hydroxy-naphthalene-3,6-disulfonic acid | red |
| 2-amino-6-(β-sulfatoethylsulfonyl)-naphthalene-8-sulfonic acid | 1-acetylamino-8-hydroxy-naphthalene-3,5-disulfonic acid | red |
| 2-amino-6-(β-sulfatoethylsulfonyl)-naphthalene-8-sulfonic acid | 1-benzoylamino-8-hydroxy-naphthalene-3,6-disulfonic acid | red |
| 2-amino-6-(β-sulfatoethylsulfonyl)-naphthalene-8-sulfonic acid | 1-benzoylamino-8-hydroxy-naphthalene-3,5-disulfonic acid | red |
| 2-amino-6-(β-sulfatoethylsulfonyl)-naphthalene-8-sulfonic acid | 2-acetylamino-5-hydroxy-naphthalene-7-sulfonic acid | orange |
| 2-amino-6-(β-sulfatoethylsulfonyl)-naphthalene-8-sulfonic acid | 3-acetylamino-5-hydroxy-naphthalene-7-sulfonic acid | scarlet |
| 2-amino-6-(β-sulfatoethylsulfonyl)-naphthalene-8-sulfonic acid | 1-(4'-sulfophenyl)-3-methyl-5-pyrazolone | yellow |
| 2-amino-6-(β-sulfatoethylsulfonyl)-naphthalene-8-sulfonic acid | 1-(4'-sulfophenyl)-3-carboxy-5-pyrazolone | yellow |
| 2-amino-6-(β-sulfatoethylsulfonyl)-naphthalene-8-sulfonic acid | 1-(4'-[2-sulfooxyethyl)phenyl]sulfonyl)-3-methyl-5-pyrazolone | yellow |
| 2-amino-6-(β-sulfatoethylsulfonyl)-naphthalene-8-sulfonic acid | N,N-bis-(2-sulfooxyethyl)-3-chloroaniline | orange |
| 2-amino-6-(β-sulfatoethylsulfonyl)-naphthalene-8-sulfonic acid | N-(2-ethanesulfonic acid)-4-methyl-6-hydroxy-pyridone | yellow |
| 2-amino-6-(β-sulfatoethylsulfonyl)-naphthalene-8-sulfonic acid | 1-hydroxynaphthalene-3,6-disulfonic acid copper complex | blue |
| 2-amino-6-(β-sulfatoethylsulfonyl)- | 1-hydroxynaphthalene-4-sulfonic acid | blue |

-continued

| Naphthylamine Base | Coupler | Shade |
|---|---|---|
| naphthalene-8-sulfonic acid | copper complex | |
| 2-amino-6-(β-sulfatoethylsulfonyl)-naphthalene-8-sulfonic acid | 1-acetylamino-8-naphthol-3,6-disulfonic acid copper complex | blue |
| 2-amino-6-(β-sulfatoethylsulfonyl)-naphthalene-8-sulfonic acid | N,N-bis(2-sulfatoethyl)-meta-chloro-aniline | orange |
| 2-amino-6-(β-sulfatoethylsulfonyl)-naphthalene-8-sulfonic acid | N,N-bis(2-sulfatoethyl) aniline | orange |
| 2-amino-6-(β-sulfatoethylsulfonyl)-naphthalene-8-sulfonic acid | 1-hydroxynaphthalene-3,6-disulfonic acid-8-(5-chloro-2,4,6-triazene-1-yl)-amino. | red |
| 2-amino-7-(β-sulfatoethylsulfonyl)-naphthalene-5-sulfonic acid | 1-acetoaceylamino-3-methyl-6-methoxy-benzene-4-sulfonic acid | yellow |
| 2-amino-7-(β-sulfatoethylsulfonyl)-naphthalene-5-sulfonic acid | 1-acetoacetylamino-3,6-dimethoxy-benzene-4-sulfonic acid | yellow |
| 2-amino-7-(β-sulfatoethylsulfonyl)-naphthalene-5-sulfonic acid | 1-hydroxynaphthalene-3,6-disulfonic acid | orange |
| 2-amino-7-(β-sulfatoethylsulfonyl)-naphthalene-5-sulfonic acid | 1-hydroxynaphthalene-4-sulfonic acid | scarlet |
| 2-amino-7-(β-sulfatoethylsulfonyl)-naphthalene-5-sulfonic acid | 1-acetylamino-8-hydroxy-naphthalene-3,6-disulfonic acid | red |
| 2-amino-7-(β-sulfatoethylsulfonyl)-naphthalene-5-sulfonic acid | 1-acetylamino-8-hydroxy-naphthalene-3,5-disulfonic acid | red |
| 2-amino-7-(β-sulfatoethylsulfonyl)-naphthalene-5-sulfonic acid | 1-benzoylamino-8-hydroxy-naphthalene-3,6-disulfonic acid | red |
| 2-amino-7-(β-sulfatoethylsulfonyl)-naphthalene-5-sulfonic acid | 1-benzoylamino-8-hydroxy-naphthalene-3,5-disulfonic acid | red |
| 2-amino-7-(β-sulfatoethylsulfonyl)-naphthalene-5-sulfonic acid | 2-acetylamino-5-hydroxy-naphthalene-7-sulfonic acid | orange |
| 2-amino-7-(β-sulfatoethylsulfonyl)-naphthalene-5-sulfonic acid | 3-acetylamino-5-hydroxy-naphthalene-7-sulfonic acid | scarlet |
| 2-amino-7-(β-sulfatoethylsulfonyl)-naphthalene-5-sulfonic acid | 1-(4'-sulfophenyl)-3-methyl-5-pyrazolone | yellow |
| 2-amino-7-(β-sulfatoethylsulfonyl)-naphthalene-5-sulfonic acid | 1-(4'-sulfophenyl)-3-carboxy-5-pyrazolone | yellow |
| 2-amino-7-(β-sulfatoethylsulfonyl)-naphthalene-5-sulfonic acid | 1-(4'-[2-sulfooxyethyl)phenyl]sulfonyl)-3-methyl-5-pyrazolone | yellow |
| 2-amino-7-(β-sulfatoethylsulfonyl)-naphthalene-5-sulfonic acid | N,N-bis-(2-sulfooxyethyl)-3-chloro-aniline | orange |
| 2-amino-7-(β-sulfatoethylsulfonyl)-naphthalene-5-sulfonic acid | N-(2-ethanesulfonic acid)-4-methyl-6-hydroxy-pyridone | yellow |
| 2-amino-7-(β-sulfatoethylsulfonyl)-naphthalene-5-sulfonic acid | 1-hydroxynaphthalene-3,6-disulfonic acid copper complex | blue |
| 2-amino-7-(β-sulfatoethylsulfonyl)-naphthalene-5-sulfonic acid | 1-hydroxynaphthalene-4-sulfonic acid copper complex | blue |
| 2-amino-7-(β-sulfatoethylsulfonyl)-naphthalene-5-sulfonic acid | 1-acetylamino-8-naphthol-3,6-disulfonic acid copper complex | blue |
| 2-amino-7-(β-sulfatoethylsulfonyl)-naphthalene-5-sulfonic acid | N,N-bis(2-sulfatoethyl) aniline | orange |
| 2-amino-7-(β-sulfatoethylsulfonyl)-naphthalene-5-sulfonic acid | 1-hydroxynaphthalene-3,6-disulfonic acid-8-(5-chloro-2,4,6-triazene-1-yl)-amino | red |

The dyestuff compounds of formula (2) and (3) can be separated from the reaction medium after their preparation, by known methods suitable for water-soluble compounds, such as, by precipitation from the reaction medium with electrolytes, such as, sodium chloride or potassium chloride, or by evaporation of the reaction medium, for example by spray-drying. When the latter method for isolation is chosen, it can be advantageous to remove sulfates if they are present in the synthesis solutions, before evaporation. This can be done by precipitation of the sulfates as calcium sulfate and filtration. In some cases, it is also possible for the solutions obtained in the synthesis to be used directly, after standardization with water, as a liquid dyestuff composition. These liquid dyestuff compositions, especially useful in chemical-pad-steam applications, show no chemical or physical changes on long term storage.

The compounds according to the invention are suitable, as water-soluble dyestuffs, for coloring (dyeing and printing) of fibers, leather or other materials containing hydroxy groups and/or amino groups. They may be used in their free acid form, as salts and in their vinylized form. Exemplary materials are natural, regenerated or synthetic, nitrogen-containing fibers and natural, regenerated or synthetic hydroxy group containing fibers. The dyestuffs according to the invention are capable of coloring these materials to deep, brilliant shades ranging from yellow to blue with superior properties. The fiber-reactive groups in the compounds of the invention can react with the NH$_2$— and OH— groups of the material, such as a cotton containing hydroxy groups, to form a covalent bond and thus form a bonded link with the fiber.

The present invention also relates to the use of the dyestuffs of the invention for coloring (such as dyeing and printing) such materials and to a process for coloring such materials. This process which comprises contacting a compound of formula (2) or (3), preferably in the form of an aqueous solution with the material and fixing the compound of formula (2) or (3) on it optionally under the action of an alkaline agent and/or heat.

Typical nitrogen-containing synthetic materials useful in this invention are polyurethanes and polyamides such as nylon 6, nylon 6/6 and nylon 11. Typical natural polyamide materials are silk and wool and other animal hair products. Typical materials containing hydroxy groups are polyvinyl alcohols, cellulosic materials such as cotton, other vegetable fibers, such as linen, hemp, jute, and their regenerated products, such as viscose rayon or cuprammonium rayon.

The novel compounds of the invention can be applied by the known application techniques for fiber-reactive dyestuffs. In general, a procedure is followed in which an aqueous solution of the compounds or their metal complex are applied to the materials, optionally in the presence of a thickener and/or other auxiliaries to improve the affinity, leveling and migration properties. After application the dyestuff is then fixed to the fiber.

The compounds of the invention are applied to natural or regenerated or synthetic polyamide fibers or polyurethane fibers or to leather by conventional techniques from an aqueous acid to aqueous neutral solution (pH range from about 3 to 6.5), usually by the exhaustion method, and are fixed on these fibers by the application of heat at a temperature between 60° and 130° C. It is possible for example to add acetic acid or acetic and ammonium acetate as a buffer to the bath containing the dyestuffs in order to obtain the desired pH value. Addition of leveling agents, for example those based on a reaction product of cyanuric chloride with three moles of an aminobenzenesulfonic acid and/or an amino-naphthalenesulfonic acid or those based on a reaction product of stearylamine and ethylene oxide, can be used for the purpose of achieving level dyeings. The compounds of the invention can be applied and fixed on the material by the exhaustion process either at the boiling point or at a higher temperature, for example, at 105° to 120° C., under pressure. It is expedient for the dyeing to be started with a slow increase in temperature to 60° C. and, after some time, for the temperature to be increased slowly to a higher temperature.

In the coloring of fiber materials containing hydroxy groups, the compound of the invention is generally applied to the fiber from a weakly acid to alkaline solution and fixed on the fiber by an alkaline agent subsequently added to the dye bath or applied directly to the fiber. Typical alkaline substances which can be used in these fixing solutions are sodium hydroxide, sodium carbonate, sodium bicarbonate, potassium hydroxide, potassium carbonate, trisodium phosphate or sodium or potassium silicate or waterglass. The dyestuffs can be applied by exhaustion dyeing procedures or the chemical pad steam (C.P.S.) process. In the exhaust method, the fiber material is treated in an aqueous-alkaline solution of the compound of the invention, preferably in the presence of an electrolyte, such as sodium chloride or sodium sulfate, at an elevated temperature between 30° and 130° C. It is preferable for the dyeing to be started at a low temperature and for the temperature of the exhaustion bath to be slowly increased to about 60° C.-130° C., and completing the fixation step in this temperature range.

In the chemicalpad-steam (C.P.S.) method, the fabric is continuously passed through a dyebath, dried, passed through an alkaline chemical pad, fixed by steaming, washed and dried. Fiber reactive dyes perform well in this application.

If the compounds of the invention are applied to the fiber material in the form of printing pastes, it is usual to employ thickeners, such as sodium alginate, cellulose ether, tragacanth or gum arabic, optionally with the addition of a printing auxiliary and an alkaline compound. These prints are then treated with hot air at a temperature between 70° and 230° C., preferably between 100° and 150° C. (thermofixed), or steamed. The compounds of invention can be applied to the fiber by customary printing processes such as a one-step procedure using a printing paste of the dyestuff containing sodium bicarbonate or one of the other alkaline agents with subsequent fixation of the compound by steaming at 101° to 103° C. They also can be applied to the fiber by a two-step process of applying a neutral or weakly acid printing paste of the dyestuff and then fixing it either by passing the printed material through a hot alkaline bath containing electrolytes. Alternatively, it can be overpadded with an alkaline liquour containing electrolytes and left to stand at room temperature but usually it is treated with heat using hot steam or hot air. If an electrolyte-containing alkaline bath is used for fixing, the bath temperature is 60° to 105° C., so that subsequent treatment by hot air or steam can be eliminated.

If the material is impregnated with the compound of the invention and treated with a strong aqueous alkali, (e.g. sodium hydroxide or potassium hydroxide and/or sodium silicate or potassium silicate or trisodium phosphate) it is sufficient for the moist goods (usually prints) to be left to stand at room temperature for a relatively long period to fix the dyestuff. The colored materials thus obtained are then after treated, rinsed and dried, in the usual manner.

To those skilled in the art to which this invention relates many changes, modifications and widely different embodiments and application of the invention will suggest themselves without departing from the spirit and scope of the invention. The disclosure and the description herein are illustrative and are not intended to be limiting.

What is claimed is:

1. A method for the preparation of a sulfonic acid isomer of a sulfonyl substituted 2-aminonaphthalene which comprises:
   (a) reacting a sulfonyl substituted 2-aminonaphthalene of the formula:

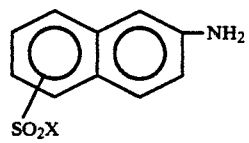

(1)

wherein
X represents the group —CH$_2$—CH$_2$—Z wherein Z represents an inorganic or organic substituent selected from halogen, hydroxy, acyloxy, wherein the term acyl is R'CO and R' is defined below dialkylamino, thiosulfato, phosphato, or sulfato, wherein the group —SO$_2$X is located at the 5, or 6, or 7, or 8 ring position;
with an anhydride of the formula R'CO—O—CO—R' or an acid chloride of the formula R'COCl wherein R' is selected from unsubstituted and substituted lower alkyl of 1 to 4 carbons and unsubstituted or substituted phenyl wherein said substituents are selected from halo, nitro, lower alkoxy, phenoxy, lower alkyl or mixtures thereof;
to form a sufonyl substituted N-2-acylaminonaphthalene of the formula:

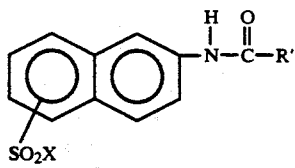

(2)

wherein R' and X are defined above;

(b) sulfonating said sulfonyl substituted N-2-acylaminonaphthalene at a temperature between 0°–50° C. whereby one positional isomeric sulfonation product in formed having the formula:

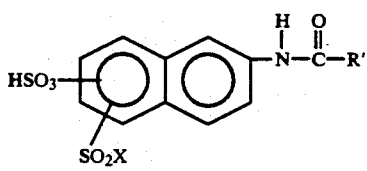

(3)

wherein the groups —SO₂X and HSO₃—, respectively have one of the following ring positional configurations:
5-7, 6-8, 7-5, or 8-6 and wherein R' and X are defined above.

2. A method according to claim 1 wherein the group —SO₂X is located at the 5 ring position and group HSO₃— is located at the 7 ring position.

3. A method according to claim 1 wherein the group —SO₂X is located at the 6 ring position and the group HSO₃— is located at the 8 ring position.

4. A method according to claim 1 wherein the group —SO₂X is located at the 7 ring position and the group HSO₃— is located at the 5 ring position.

5. A method according to claim 1 wherein the group —SO₂X is located at the 8 ring position and the group HSO₃— is located at the 6 ring position.

6. A method according to claims 1, 2, 3, 4 or 5 wherein said sulfonation is conducted by reacting said N-acyl-aminophthalene of the formula (2) with a sulfonating agent selected from oleum, chlorosulfonic acid or sulfur trioxide.

7. A method for the preparation of a sulfonic acid isomer of a sulfonyl substituted, N-2-acylaminonaphthalene which comprises: sulfonating at a temperature of 0° to 50° C. a sulfonyl substituted, N-2-acylaminonaphthalene of the formula:

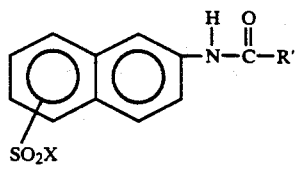

(2)

wherein X represents the group —CH₂—CH₂—Z; wherein Z represents an inorganic or organic substituent selected from halogen, hydroxy, acyloxy, wherein the term acyl is R'CO and R' is defined below dialkyamino, thiosulfato, phosphato, or sulfato; wherein R' is selected from substituted or unsubstituted lower alkyl of 1 to 4 carbons and unsubstituted or substituted phenyl; wherein said substitutents are selected from halo, nitro, lower alkyl, lower alkoxy, phenoxy, or mixtures thereof; whereby one positional isomeric sulfonation product is formed of the formula:

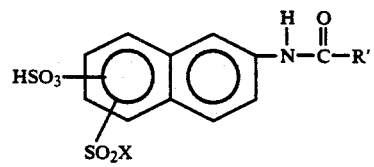

(3)

wherein the groups —SO₂X and HSO₃— respectively have one of the following ring positional configurations 5-7, 6-8, 7-5 or 8-6 and wherein R' and X are defined above.

8. A method according to claim 7 wherein the group —SO₂X is located at the 5 ring position and group HSO₃— is located at the 7 ring position.

9. A method according to claim 7 wherein the group —SO₂X is located at the 6 ring position and the group HSO₃— is located at the 8 ring position.

10. A method according to claim 7 wherein the group —SO₂X is located at the 7 ring position and the group HSO₃— is located at the 5 ring position.

11. A method according to claim 7 wherein the group —SO₂X is located at the 8 ring position and the group HSO₃— is located at the 6 ring position.

12. A method according to claims 7, 8, 9, 10 or 11 wherein said sulfonation is conducted by reacting said N-2-acylaminonaphthalene of the formula (2) with a sulfonating agent selected from oleum, chloro sulfonic acid or sulfur trioxide.

* * * * *